(12) United States Patent
Sun et al.

(10) Patent No.: US 10,829,741 B2
(45) Date of Patent: *Nov. 10, 2020

(54) METHOD FOR PREPARING FOOT-AND-MOUTH DISEASE VIRUS-LIKE PARTICLES

(71) Applicant: Lanzhou Veterinary Research Institute Chinese Academy of Agricultural Sciences, Lanzhou (CN)

(72) Inventors: Shiqi Sun, Lanzhou (CN); Huichen Guo, Lanzhou (CN); Yun Zhang, Lanzhou (CN); Yanyan Chang, Lanzhou (CN); Yanquan Wei, Lanzhou (CN); Jiaxi Ru, Lanzhou (CN); Xiaoying Zhi, Lanzhou (CN); Ping Du, Lanzhou (CN); Xiangtao Liu, Lanzhou (CN); Hong Yin, Lanzhou (CN); Jianxun Luo, Lanzhou (CN)

(73) Assignee: LANZHOU VETERINARY RESEARCH INSTITUTE CHINESE ACADEMY OF AGRICULTURAL SCIENCES, Lanzhou (CN)

(*) Notice: Subject to any disclaimer, the term of this patent is extended or adjusted under 35 U.S.C. 154(b) by 12 days.

This patent is subject to a terminal disclaimer.

(21) Appl. No.: 15/993,637

(22) Filed: May 31, 2018

(65) Prior Publication Data
US 2019/0367885 A1 Dec. 5, 2019

(51) Int. Cl.
*C12N 7/04* (2006.01)
*C12N 7/00* (2006.01)
*G01N 33/569* (2006.01)

(52) U.S. Cl.
CPC ............... *C12N 7/00* (2013.01); *C12N 7/045* (2013.01); *G01N 33/56983* (2013.01); *C12N 2770/32122* (2013.01); *C12N 2770/32131* (2013.01); *C12N 2770/32152* (2013.01); *G01N 2333/09* (2013.01); *G01N 2333/395* (2013.01); *G01N 2800/26* (2013.01)

(58) Field of Classification Search
None
See application file for complete search history.

(56) References Cited

FOREIGN PATENT DOCUMENTS

CN 106479986 * 3/2017

* cited by examiner

*Primary Examiner* — Nicole Kinsey White
(74) *Attorney, Agent, or Firm* — Matthias Scholl P.C.; Matthias Scholl

(57) ABSTRACT

A method for preparing serotype O foot-and-mouth disease virus-like particles, the method including: construction of small ubiquitin-like modifier fusion expression vector, construction of recombinant expression vectors, construction of recombinant co-expression vector, expression and purification of proteins, and in-vitro assembly of serotype O foot-and-mouth disease virus-like particles. The disclosure also provides a test strip for detecting serotype O foot-and-mouth disease including a bottom board, and a detection layer disposed on the top of the bottom board. A detection line and a control line are disposed on the detection layer. An absorbent layer is disposed at one end of the detection layer close to the control line, and an immuno-gold pad is disposed at the other side of the detection layer close to the detection line. A sample pad is disposed on the top of the immuno-gold pad.

2 Claims, 1 Drawing Sheet
Specification includes a Sequence Listing.

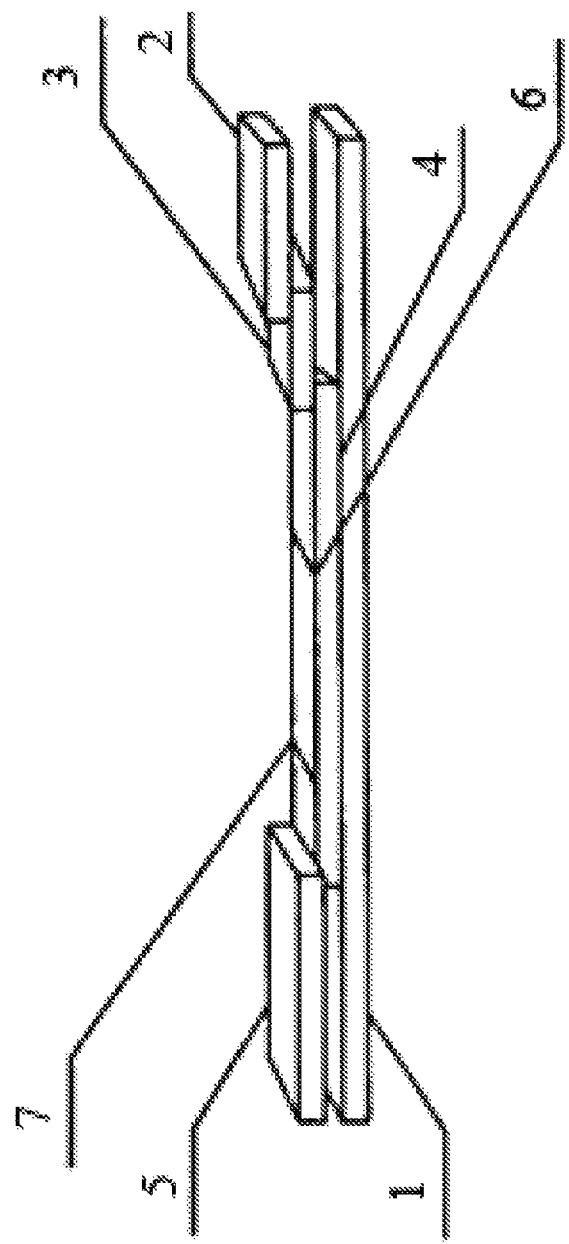

SEQUENCE LISTING

```
<160> NUMBER OF SEQ ID NOS: 10

<210> SEQ ID NO 1
<211> LENGTH: 51
<212> TYPE: DNA
<213> ORGANISM: Artificial Sequence
<220> FEATURE:
<223> OTHER INFORMATION: Fully synthetic

<400> SEQUENCE: 1
gccatgggtc atcaccatca tcatcacggg tcggactcag aagtcaatca a        51

<210> SEQ ID NO 2
<211> LENGTH: 44
<212> TYPE: DNA
<213> ORGANISM: Artificial Sequence
<220> FEATURE:
<223> OTHER INFORMATION: Fully synthetic

<400> SEQUENCE: 2
ggatccgaga ccttaaggtc tcaacctcca atctgttcgc ggtg                44

<210> SEQ ID NO 3
<211> LENGTH: 38
<212> TYPE: DNA
<213> ORGANISM: Artificial Sequence
<220> FEATURE:
<223> OTHER INFORMATION: Fully synthetic

<400> SEQUENCE: 3
tacttcgtct ccgcggatcc ggagccgggc aatccagc                       38

<210> SEQ ID NO 4
<211> LENGTH: 41
<212> TYPE: DNA
<213> ORGANISM: Artificial Sequence
<220> FEATURE:
<223> OTHER INFORMATION: Fully synthetic

<400> SEQUENCE: 4
gcgagtggat ccattaagct tgcctccttc gaggggagtt c                   41

<210> SEQ ID NO 5
<211> LENGTH: 32
<212> TYPE: DNA
<213> ORGANISM: Artificial Sequence
<220> FEATURE:
<223> OTHER INFORMATION: Fully synthetic

<400> SEQUENCE: 5
ggacttcgtc tcactactgc caccggggaa tc                             32

<210> SEQ ID NO 6
```

```
<211> LENGTH: 34
<212> TYPE: DNA
<213> ORGANISM: Artificial Sequence
<220> FEATURE:
<223> OTHER INFORMATION: Fully synthetic

<400> SEQUENCE: 6
gcttatggat ccttacagga gttgttttgc tggg                              34

<210> SEQ ID NO 7
<211> LENGTH: 31
<212> TYPE: DNA
<213> ORGANISM: Artificial Sequence
<220> FEATURE:
<223> OTHER INFORMATION: Fully synthetic

<400> SEQUENCE: 7
gcacttcgtc tcgcgattgt cccggttgca t                                 31

<210> SEQ ID NO 8
<211> LENGTH: 32
<212> TYPE: DNA
<213> ORGANISM: Artificial Sequence
<220> FEATURE:
<223> OTHER INFORMATION: Fully synthetic

<400> SEQUENCE: 8
gcgcacggat ccttgtgagc gggggtcaat cg                                32

<210> SEQ ID NO 9
<211> LENGTH: 31
<212> TYPE: DNA
<213> ORGANISM: Artificial Sequence
<220> FEATURE:
<223> OTHER INFORMATION: Fully synthetic

<400> SEQUENCE: 9
gcaattggac ccgtccggcg tagaggatcg a                                 31

<210> SEQ ID NO 10
<211> LENGTH: 33
<212> TYPE: DNA
<213> ORGANISM: Artificial Sequence
<220> FEATURE:
<223> OTHER INFORMATION: Fully synthetic

<400> SEQUENCE: 10
gcgcacctcg agctactgtt gccgagcgtc cac                               33
```

METHOD FOR PREPARING FOOT-AND-MOUTH DISEASE VIRUS-LIKE PARTICLES

CROSS-REFERENCE TO RELATED APPLICATIONS

The contents of Chinese Patent Application No. 201611081557.8 filed Nov. 30, 2016 and any intervening amendments thereto are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND

The disclosure relates to the technical field of serological detection, and more particularly to a method for preparing serotype O foot-and-mouth disease virus (FMDV)-like particles, and a test strip for detecting serotype O foot-and-mouth disease.

Conventional methods for detecting antibodies against serotype O FMDV include complement fixation test (CFT), virus neutralization test (VNT), agglutination test, immunodiffusion, and enzyme-linked immunosorbent assay (ELISA). These methods are susceptible to external factors and require stringent laboratory conditions.

SUMMARY

Disclosed is a method for preparing serotype O foot-and-mouth disease virus-like particles and a test strip for detecting serotype O foot-and-mouth diseases that can shorten the detection period. Experiments are performed in a biosafety level 3 laboratory.

Disclosed is a method for preparing serotype O foot-and-mouth disease virus-like particles, the method comprising:

S1: amplifying a smt3 gene from a genome of *Saccharomyces cerevisiae* strain EGY48, enzymatically cleaving the smt3 gene and a pET-28a vector using Nco I and BamH I, inserting the cleaved smt3 gene into the cleaved pET-28a vector, to obtain a small ubiquitin-like modifier (SUMO) fusion expression vector pSM1, and replacing a kanamycin resistance gene of the pSM1 by an ampicillin resistance gene, to obtain a SUMO fusion expression vector pSM2;

S2:
  S2.1: designing primers according to the porcine serotype O FMDV deposited in GenBank, extracting the viral RNA from the porcine serotype O FMDV, and performing reverse transcription and amplification to yield the genes VP0, VP3, and VP1; and
  S2.2: enzymatically cleaving the genes VP0, VP3, and VP1 using BsmB I/BamH I respectively to yield corresponding fragments, enzymatically cleaving the vectors pSM1, pSM2, and pSM1 using Bsa I, inserting the fragments into the cleaved vectors pSM1, pSM2, and pSM1, to obtain recombinant expression vectors pSM1/VP0, pSM2/VP3, and pSM1/VP1;

S3: acquiring a DNA fragment comprising prokaryotic expression elements comprising 17 promoter and VP1 gene through amplification with pSM1/VP1 as a template and using T7BamH I/VP1Xho I as primers, enzymatically cleaving the DNA fragment and the recombinant expression vector pSM1/VP0 using BamH I/Xho I, inserting the cleaved DNA fragment into the cleaved recombinant expression vector pSM1/VP0, to obtain a recombinant co-expression vector pSM1/VP0-VP1;

S4:
  S4.1: co-transforming the positive recombinant plasmids pSM2/VP3 and pSM1/VP0-VP1 that are precisely sequenced into the competent cells BL21-CodonPlus (DE3)-RIL, picking a monoclonal colony, and inoculating and culturing the monoclonal colony in a medium containing ampicillin, kanamycin and chloramphenicol; and
  S4.2: adding IPTG to a bacterial suspension in the medium at a concentration of 0.5 mmol/L, allowing inducible expression for 16 hrs, collecting bacterial cells from the bacterial suspension, suspending the bacterial cells in a buffer, and centrifuging to obtain recombinant proteins; and S5: removing the small ubiquitin-like modifier using HisTrap HP, collecting a liquid containing VP0, VP1, and VP3, dialyzing against the dialysis buffer PBS, and assembling to yield serotype O foot-and-mouth disease virus-like particles.

The diameter of the serotype O foot-and-mouth disease virus-like particles is 18-21 nm.

Also disclosed is a test strip for detecting serotype O foot-and-mouth disease comprising a bottom board, and a detection layer disposed on the top of the bottom board. A detection line and a control line are disposed on the detection layer; and an absorbent layer is disposed at one end of the detection layer close to the control line, and an immuno-gold pad is disposed at the other side of the detection layer close to the detection line. A sample pad is disposed on the top of the immuno-gold pad.

The immuno-gold pad is coated with colloidal gold particles that are conjugated with a SPA marker, the detection line is coated/impregnated with serotype O foot-and-mouth disease virus-like particles, and the control line is coated/impregnated with rabbit IgG.

The ratio of the colloidal gold to SPA on the immuno-gold pad can be $2\times10^4$:1-2.

The ratio of the colloidal gold to SPA on the immuno-gold pad can be $2\times10^4$:1.3.

The adsorption rate of the immuno-gold pad can be 10-50 μL/cm.

The detection line can be coated/impregnated with 0.5-1 mg/mL of serotype O foot-and-mouth disease virus-like particles.

The control line can be coated/impregnated with 0.8-1.5 mg/mL of immune rabbit serum IgG.

Advantages of the method in the disclosure are summarized as below:

Compared with conventional CFT, VNT, agglutination test, immunodiffusion and ELISA, the method of the disclosure is accurate, stable, inexpensive, efficient, and easy to operate, and can be carried out in normal conditions.

BRIEF DESCRIPTION OF THE DRAWINGS

The invention is described hereinbelow with reference to accompanying drawings, in which the sole FIGURE is a schematic structural diagram of a test strip for detecting serotype O foot-and-mouth disease according to an embodiment of the disclosure.

In the drawings, the following reference numbers are used: 1—bottom board, 2—sample pad, 3—immuno-gold pad, 4—detection layer, 5—absorbent layer, 6—detection line, 7—control line.

DETAILED DESCRIPTION

The disclosure provides a method for preparing serotype O foot-and-mouth disease virus-like particles, the method comprising the following steps:

S1: Construction of Small Ubiquitin-Like Modifier Fusion Expression Vector pSM a. The smt3 gene (GenBank Accession No: AY558174) is amplified from the genome of *Saccharomyces cerevisiae* strain EGY48 by using the primer sequences that comprise an upstream primer smt3F: 5'GCCATGGGTCATCACCAT-CATCATCAC (6× His) GGGTCG GACTCAGAAGT-CAATCAA 3' (SEQ ID NO. 1); and a downstream primer smt3F: 5'GGATCCGAGACCTTAAGGTCTCAACCTC-CAATCTGTTCGCGGTG 3' (SEQ ID NO. 2).

b. The smt3 gene that are enzymatically cleaved by Nco I and BamH I (both of which are a restriction endonucleases) are inserted into the pET-28a vector that are also enzymatically cleaved by Nco I and BamH I to obtain the vector pSM1, and the kanamycin resistance gene in the pSM1 is replaced by the ampicillin resistance gene, to obtain the vector pSM2.

S2: Construction of Recombinant Expression Vectors

S201: Amplification of structural protein VP0, VP3, and VP1 encoding genes of serotype O foot-and-mouth disease virus—The primers are designed according to the porcine serotype O FMDV deposited in GenBank. The viral RNA is extracted from the porcine serotype O FMDV by using the RNaeasy Mini kit commercially available from Qiagen, and the VP0, VP3, and VP1 gene are obtained respectively by amplification after reverse transcription. The PCR cycling parameters during the reverse transcription comprise: 1 cycle of 5 min at 94° C., 30 cycles of 60 s at 94° C., 60 s at 58° C., and 2.5 min at 72° C., followed by the last cycle of 8 min at 72° C.

Primer Sequences:

```
Upstream primer VP0-F BsmB I:
SEQ ID NO. 3:
5'TACTTCGTCTCCGCGGATCCGGAGCCGGGCAATCCAGC;

Downstream primer VP0-RBamH I:
SEQ ID NO. 4:
5'GCGAGTGGATCCATTAAGCTTGCCTCCTTCGAGGGGAGTTC;

Upstream primer VP1-F BsmB I:
SEQ ID NO. 5:
5' GGACTTCGTCTCACTACTGCCACCGGGGAATC;

Downstream primer VP1-R BamH I:
SEQ ID NO. 6:
5'GCTTATGGATCCTTACAGGAGTTGTTTTGCTGGG Upstream primer VP3-F BsmB I:
SEQ ID NO. 7:
5'GCACTTCGTCTCGCGATTGTCCCGGTTGCAT;

Downstream primer VP3-R BamH I:
SEQ ID NO. 8:
5'GCGCACGGATCCTTGTGAGCGGGGGTCAATCG.
```

S202: The VP0, VP3, and VP1 fragments that are enzymatically cleaved by BsmB I/BamH I (both of which are a restriction endonucleases) are inserted respectively into the pSM1, pSM2, and pSM1 that are enzymatically cleaved by Bsa I, to obtain the recombinant expression vectors pSM1/VP0, pSM2/VP3, and pSM1/VP1.

S3: Construction of Recombinant Co-Expression Vector:

A DNA fragment comprising prokaryotic expression elements comprising T7 promoter and VP1 gene is obtained by amplification with pSM1/VP1 as a template and using T7BamH I/VP1Xho I as primers. The DNA fragment that is enzymatically cleaved by BamH I/Xho 1 and inserted into the pSM1/VP0 that is also enzymatically cleaved by BamH I/Xho 1, to obtain the recombinant co-expression vector pSM1/VP0-VP1. The primer sequences comprise an upstream primer T7BamH I: 5'GCAATTGGA CCCGTC-CGGCGTAGAGGATCGA (SEQ ID NO. 9), and a downstream primer VP1Xho 1: 5'GCGCACCTCGAGCTACT-GTTGCCGAGCGTCCAC (SEQ ID NO. 10).

S4: Expression and Purification of Proteins

The positive recombinant plasmids pSM2/VP3 and pSM1/VP0-VP1 that are precisely sequenced are co-transformed into the competent cells BL21-CodonPlus (DE3)-RIL. A monoclonal colony is picked and inoculated into an LB medium containing ampicillin, kanamycin and chloramphenicol, and cultured for 12 hrs at a temperature of 37° C. and a rotational speed of 220 rpm. Then the cultured expression bacteria are further 1:100 inoculated into 200 mL of the LB medium containing ampicillin, kanamycin and chloramphenicol again, and cultured at a temperature of 37° C. and a rotational speed of 220 rpm until the OD600 reaches about 0.9. 1 ml is sampled and used as a pre-induction control.

The remaining bacterial suspension is stood at 16° C., and added with isopropyl thiogalactoside (IPTG) at a concentration of 0.5 mmol/L to induce the expression for 16 hrs. The bacterial suspension after induction is centrifuged for 20 min at a rotational speed of 4750 rpm. The bacterial cells are collected, then 1:50 suspended in a buffer A (having a composition of 500 mmol/L NaCl, 20 mmol/L Tris-HCl, 20 mmol/L Imidazole, 2 mmol/L DTT, and 0.05% TritonX-100, pH 8.4), mixed fully, ultrasonicated on ice for 6 min, and then centrifuged for 15 min at 11 500×g at 4° C. The supernatant is collected, to obtain the recombinant proteins.

Purification of recombinant proteins by using His-tag Protein Purification Kit: The recombinant protein sample is subjected to 10% SDS-PAGE electrophoresis. Then the recombinant proteins are transferred to a polyvinylidene difluoride (PVDF) film by wet transfer, blocked for 1 hr at 37° C. with a blocking buffer (PBS containing 5% skimmed milk powder, pH 7.0), incubated for 1 hr at 37° C. with anti-His primary antibody (at a molar ratio of 1:3000) and anti-FLAG primary antibody respectively, washed fully with PBST (a buffer), incubated for 1 hr at 37° C. with horse-radish peroxidase conjugated rabbit anti-mouse IgG (at a molar ratio of 1:6000) and goat anti-rabbit IgG (at a molar ratio of 1:4000) respectively, washed fully with PBST, added with a luminescent substrate and reacted for 3 min in dark, exposed under a Kozak film, developed, and fixed, to observe the expression of proteins of interest. It is found through observation that the proteins of expected sizes are obtained by this method, and the proteins are immunologically active.

S5: In-Vitro Assembly of Serotype O Foot-and-Mouth Disease Virus-Like Particles

The small ubiquitin-like modifier is removed by using HisTrap HP following the instruction for use of the reagent provided by Invitrogen, and a liquid containing VP0, VP1, and VP3 is collected, and dialyzed against the dialysis buffer PBS (pH 7.5). Then, VP0, VP1, and VP3 are assembled into serotype O foot-and-mouth disease virus-like particles. The virus-like particles are observed under an electron microscope, and a plurality of virus-like particles having a diameter of 18-21 nm can be clearly observed, indicating that virus particles are obtained successfully by assembly outside a prokaryote.

Referring to the sole FIGURE, an embodiment of the disclosure provides a test strip for detecting serotype O foot-and-mouth disease in an animal. The test strip comprises a bottom board 1 made from PVC, and a detection layer 4 disposed on the top of the bottom board 1. A detection line 6 and a control line 7 are disposed on the detection layer 4, and an absorbent layer 5 is disposed at one end of the detection layer close to the control line 7, and an immuno-gold pad 3 is disposed at the other side of the detection layer 4 close to the detection line 7. A sample pad 2 is disposed on the top of the immuno-gold pad 3.

The immuno-gold pad 3 comprises colloidal gold particles that are conjugated with a *Staphylococcus* Protein A (SPA) marker, the detection line 6 is coated/impregnated with serotype O foot-and-mouth disease virus-like particles, and the control line 7 is coated/impregnated with rabbit IgG.

The ratio of the colloidal gold to SPA on the immuno-gold pad 3 is $2\times10^4$:1-2, and most preferably $2\times10^4$:1.3. The adsorption rate of the immuno-gold pad 3 is 10-50 μL/cm.

The detection line 6 is coated/impregnated with 0.5-1 mg/mL of serotype O foot-and-mouth disease virus-like particles, and the control line 7 is coated/impregnated with 0.8-1.5 mg/mL of immune rabbit serum IgG.

A method for preparing the test strip for detecting serotype O foot-and-mouth disease in an animal comprises the following steps.

S1: Preparation of IgG a. The whole blood is sampled from 2 negative rabbits, and precipitated overnight in a freezer at 4° C. The precipitated whole blood is centrifuged for 10 min at a rotational speed of 4000 rpm, and the supernatant is collected that is serum. 20 mL of the serum is added to 20 mL of saline, and then 10 mL of a saturated $(NH_4)_2SO_4$ solution is added, mixed until uniform, stood for 30 min, and centrifuged for 20 min at a rotational speed of 3000 rpm. The pellet is discarded to remove the fibrin, and the supernatant is collected.

b. 30 mL of a saturated $(NH_4)_2SO_4$ solution is added to the supernatant, mixed until uniform, stood for 30 min, and centrifuged for 20 min at a rotational speed of 3000 rpm. The supernatant is discarded, and the pellet is collected. 20 mL of saline and 10 mL of a saturated $(NH_4)_2SO_4$ solution is added to the pellet, mixed until uniform, stood for 30 min, and centrifuged for 20 min at a rotational speed of 3000 rpm. The supernatant is discarded.

Step b is repeated 2-3 times, 10 mL of saline is added to the purified pellet, followed by dialysis. The dialysis is performed overnight in pure water initially for salt removal, and then in saline at 4° C. for 24 hrs, during which the dialysis fluid is changed once every 2-3 hrs.

Whether the dialysis is complete is detected as follows. The detection reagent is 1% $BaCl_2$ (for the detection of $SO_4^{2-}$) or Nessler's Reagent (for the detection of $NH_4^+$). 1-2 drops of the detection reagent are added to 3-4 mL of the dialysate. If the solution appears brick red, $NH_4^+$ is considered to be present; and if a white precipitate is produced, $SO_4^{2-}$ is considered to be present. After dialysis to such an extent that no precipitate is produced, the precipitate is removed by centrifugation (to remove the miscellaneous proteins), and the supernatant is the purified rabbit IgG.

S2: Preparation of the colloidal gold: 1 g of aurichlorohydric acid is dissolved in 100 mL of triple distilled water to prepare a 1% aurichlorohydric acid solution. 1 mL of 1% aurichlorohydric acid solution in water is added to 100 mL of water, and heated to boiling. 1.7 mL of 1% trisodium citrate solution in water is added dropwise with stirring, and boiled for another 5 min. After cooling, distilled water is added to 100 mL. In this way, colloidal gold is obtained, which is stored at 4° C.

S3: Determination of the minimum dosage of SPA: 100 μL of the colloidal gold is added respectively to each well of a 96-well plate. Then 1-20 μL of 0.05 mg/mL SPA is added respectively to each well, mixed uniformly, and stood for 15 min. 20 μL of 10% NaCl is added respectively to each well, and stood for 10 min. The volume of SPA added to the well that is maintained to be red is the minimum protein dosage, and an optimum marker dosage is obtained by a 30% increase on this basis. In this embodiment, the minimum protein dosage is 10 μL, that is, each 100 μL of 1 g/100 mL colloidal gold requires 10 μL of 0.05 mg/mL SPA. The weight ratio of the colloidal gold to SPA is $2\times10^4$:1, and most preferably $2\times10^4$:1.3. In practical use, the ratio of the colloidal gold to SPA can be adjusted as desired.

S4: Preparation of SPA modified colloidal gold and immuno-gold pad 3: The colloidal gold is adjusted to pH 5.9 with 0.1 M $K_2CO_3$, and corresponding SPA solution is added to the colloidal gold at a weight ratio of $2\times10^4$:1-1.5 (most preferably $2\times10^4$:1-1.3), stood for 30 min, and then centrifuged for 30 min at a rotational speed of 10000 rpm at a temperature of 4° C. The pellet is dissolved in a re-suspending solution and mixed uniformly to obtain a SPA modified colloidal gold solution. A glass film is used as a substrate of the immuno-gold pad 3. The glass film is immersed in the SPA modified colloidal gold solution and air dried. The adsorption rate is 10-50 μL/cm, and most preferably 30 μL/cm. In this manner, the immuno-gold pad 3 is obtained.

S5: Preparation of detection layer 4

A nitrocellulose membrane is used as a substrate of the detection layer 4. The detection line 6 and the control line 7 are marked on the detection layer 4, in which the detection line 6 is 0.3-1 cm (and most preferably 0.5 cm) away from the control line 7, and the control line 7 is located in a middle section of the nitrocellulose membrane. 0.5-1 mg/mL (and most preferably 0.8 mg/mL) serotype O foot-and-mouth disease virus-like particles are coated on the detection line 6; and rabbit IgG is coated on the control line 7 in an amount of 10 μL/1 cm.

S6: Preparation of the sample pad 2: A glass fiber membrane is used as a substrate of the sample pad 2. 20 mM phosphate buffer (PB), 1% Tween 20, 1% BSA, and 2.5% sucrose are dissolved in 100 mL of triple distilled water, and filtered to obtain a sample solution. The glass fiber membrane is soaked in the sample solution, removed, and air dried after fully impregnation.

S7: The detection layer 4 is disposed on the top of the bottom board 1, and pressed flat. A portion of the absorbent layer 5 (absorbent paper) is fixed onto the bottom board 1, and the other portion is fixed onto the detection layer 4 at the side close to the control line 7. A portion of the immuno-gold pad 3 is fixed onto the bottom board 1, and the other portion is fixed onto the detection layer 4 at the side close to the detection line 6. A portion of the sample pad 2 is fixed onto the bottom board 1, and the other portion is fixed onto the immuno-gold pad 3.

During the use of the colloidal gold test strip according to the disclosure, the sample is diluted first, and then the end with the sample pad 2 of the colloidal gold test strip is inserted into the sample. The sample pad 2 is provided with a liquid level mark, and the liquid level of the sample cannot go over the liquid level mark. After the absorbent layer 5 is completely wetted with the liquid, the test strip is taken out, laid flat for 5-15 min, and then observed.

If the blood sample contains an antibody against serotype O foot-and-mouth disease virus, the antibody in the blood sample binds to the SPA modified colloidal gold in the immuno-gold pad 3 to form a complex, and then to the serotype O foot-and-mouth disease virus-like particles on the detection line 6 to form a mauve line, and then keeps on moving, such that the recombinant protein SPA carried by the antibody not binding to the antigen binds to the IgG antibody on the control line 7, to form a mauve line.

If no mauve line is shown at the control line 7, it indicates that the test strip is invalid. If the blood sample does not contain relevant antibody against serotype O foot-and-mouth disease virus, no mauve line is shown at the detection line 6, and a mauve line is still shown at the control line 7.

Unless otherwise indicated, the numerical ranges involved include the beginning and end values. It will be obvious to those skilled in the art that changes and modifications may be made, and therefore, the aim in the appended claims is to cover all such changes and modifications.

What is claimed is:

1. A method for preparing serotype 0 FMDV-like particles, the method comprising:
1) amplifying a smt3 gene from a genome of *Saccharomyces cerevisiae* strain EGY48, enzymatically cleaving the amplified smt3 gene and a pET-28a vector using Nco I and BamH I, inserting the cleaved smt3 gene into the cleaved pET-28a vector to obtain a small ubiquitin-like modifier (SUMO) fusion expression vector pSM1, and replacing the kanamycin resistance gene of the pSM1 with an ampicillin resistance gene to obtain a SUMO fusion expression vector pSM2;
2) designing primers based on a porcine serotype 0 FMDV, extracting a viral RNA from the porcine serotype 0 FMDV, and performing reverse transcription and amplification to yield genes VP0, VP3, and VP1, wherein an upstream primer and a downstream primer for VP0 amplification have sequences of SEQ ID NO: 3 and SEQ ID NO: 4, respectively; an upstream primer and a downstream primer for VP3 amplification have sequences of SEQ ID NO: 7 and SEQ ID NO: 8, respectively; and an upstream primer and a downstream primer for VP1 amplification have sequences of SEQ ID NO: 5 and SEQ ID NO: 6, respectively; the upstream primer for VP0 amplification, the upstream primer for VP3 amplification, and the upstream primer for VP1 amplification each comprise a BsmB I restriction site; and the downstream primer for VP0 amplification, the downstream primer for VP3 amplification, and the downstream primer for VP1 amplification each comprise a BamH I restriction site;
3) enzymatically cleaving the genes VP0, VP3, and VP1 using BsmB I/BamH I respectively to yield corresponding fragments, enzymatically cleaving the vectors pSM1, pSM2, and pSM1 using Bsa I, inserting the fragments into the cleaved vectors pSM1, pSM2, and pSM1 to obtain recombinant expression vectors pSM1/VP0, pSM2/VP3, and pSM1/VP1, respectively, wherein the recombinant expression vectors pSM1/VP0, pSM2/VP3, and pSM1/VP1 each comprise the smt3 gene;

4) performing amplification by using the recombinant expression vector pSM1/VP1 as a template and T7BamH I primer and VP1Xho I primer to obtain a DNA fragment, wherein the DNA fragment comprises the VP1 gene and a prokaryotic expression element, the prokaryotic expression element comprises a T7 promoter; the T7BamH I primer has a sequence of SEQ ID NO: 9; and the VP1Xho I primer has a sequence of SEQ ID NO: 10;

5) enzymatically cleaving the DNA fragment from 4) and the recombinant expression vector pSM1/VP0 using BamH I/Xho I, inserting the cleaved DNA fragment into the cleaved recombinant expression vector pSM1/VP0 to obtain a recombinant co-expression vector pSM1/VP0-VP1;

6) co-transforming the recombinant expression vector pSM2/VP3 from 3) and the recombinant co-expression vector pSM1/VP0-VP1 from 5) into competent cells BL21-CodonPlus (DE3)-RIL, picking a monoclonal colony, and inoculating and culturing the monoclonal colony in a medium containing ampicillin, kanamycin, and chloramphenicol to obtain a bacterial suspension;

7) adding isopropyl β-D-1-thiogalactopyranoside(IPTG) to the bacterial suspension at a concentration of 0.5 mmol/L, allowing bacterial expression for 16 hrs, collecting bacterial cells from the bacterial suspension, suspending the bacterial cells in a buffer, ultrasonicating the bacterial cells, and centrifuging to obtain the recombinant proteins in the supernatant; and 8) purifying the recombinant proteins of 7) and collecting a liquid comprising VP0, VP1, and VP3 proteins, dialyzing the liquid against the dialysis buffer PBS to assemble the VP0, VP1, and VP3 proteins to yield serotype 0 FMDV-like particles.

2. The method of claim 1, wherein the diameter of the serotype 0 FMDV-like particles is 18-21 nm.

* * * * *